(12) United States Patent
Stamets

(10) Patent No.: US 6,660,290 B1
(45) Date of Patent: Dec. 9, 2003

(54) MYCOPESTICIDES

(75) Inventor: Paul Edward Stamets, Shelton, WA (US)

(73) Assignee: Myco Pesticides LLC, Grand Rapids, MI (US)

( * ) Notice: Subject to any disclaimer, the term of this patent is extended or adjusted under 35 U.S.C. 154(b) by 0 days.

(21) Appl. No.: 09/678,141

(22) Filed: Oct. 3, 2000

(51) Int. Cl.$^7$ .......................... A01N 25/32; A01N 63/04
(52) U.S. Cl. ..................... 424/406; 424/84; 424/93.5; 424/795.15; 424/405; 424/407; 424/409; 424/413; 424/418; 424/488; 435/179; 435/254.1
(58) Field of Search ................... 424/405, 409, 424/417, 274.1, 265.1, 93.5, 195.15; 435/173.8, 174, 177, 254.1, 179

(56) References Cited

U.S. PATENT DOCUMENTS

| | | | |
|---|---|---|---|
| 2,176,423 A | | 10/1939 | Jaeger |
| 3,070,495 A | | 12/1962 | Esenther |
| 3,249,492 A | | 5/1966 | Lund |
| 3,249,493 A | | 5/1966 | Lund |
| 3,249,494 A | | 5/1966 | Lund |
| 4,363,798 A | | 12/1982 | D'Orazio |
| 4,530,834 A | | 7/1985 | McCabe |
| 4,921,703 A | * | 5/1990 | Higuchi et al. ............. 424/419 |
| 4,925,663 A | | 5/1990 | Stimac |
| 4,942,030 A | | 7/1990 | Osborne |
| 5,057,315 A | | 10/1991 | Gunner |
| 5,057,316 A | | 10/1991 | Gunner |
| 5,141,744 A | * | 8/1992 | Chang et al. ................ 424/93 |
| 5,165,929 A | | 11/1992 | Howell |
| 5,189,831 A | | 3/1993 | Miller |
| 5,273,749 A | | 12/1993 | Bok |
| 5,310,552 A | | 5/1994 | Gunner |
| 5,360,607 A | * | 11/1994 | Eyal et al. ................. 424/93.5 |
| 5,413,784 A | | 5/1995 | Wright et al. |
| 5,418,164 A | * | 5/1995 | Andersch et al. ........ 435/254.1 |
| 5,427,784 A | | 6/1995 | Gunner |
| 5,512,280 A | | 4/1996 | Johal |
| 5,589,390 A | * | 12/1996 | Higuchi et al. .......... 435/307.1 |
| 5,595,746 A | | 1/1997 | Milner et al. |
| 5,679,362 A | | 10/1997 | Miller |
| 5,683,689 A | | 11/1997 | Stimac et al. |
| 5,728,573 A | | 3/1998 | Sugiura et al. |
| 5,804,208 A | | 9/1998 | Andersch |
| 5,882,670 A | | 3/1999 | Wada |
| 5,885,598 A | | 3/1999 | Knauf |
| 5,888,989 A | | 3/1999 | Kern |
| 5,939,065 A | | 8/1999 | Bradley |
| 5,974,726 A | | 11/1999 | Creeger |
| 5,983,558 A | | 11/1999 | Las |
| 5,989,898 A | | 11/1999 | Jin et al. |
| 6,203,811 B1 | | 3/2001 | McPherson |
| 6,254,864 B1 | | 7/2001 | Stimac |
| 6,261,553 B1 | | 7/2001 | Bradley |
| 6,280,723 B2 | | 8/2001 | Stimac |
| 6,344,191 B2 | | 2/2002 | Landolt |
| 6,416,752 B1 | | 7/2002 | Richardson |
| 2001/0006632 A1 | | 7/2001 | Stimac |
| 2001/0023552 A1 | | 9/2001 | Fujimoto |

FOREIGN PATENT DOCUMENTS

| | | |
|---|---|---|
| AU | PCT/AU92/00629 | 5/1993 |
| CA | PCT/CA01/00583 | 11/2001 |
| DE | 2617892 A1 | 12/1976 |
| DE | 2617892 A1 | 12/1976 |
| EP | 0335023 | 10/1989 |
| EP | 0406103 A1 | 1/1991 |
| EP | 0494592 A1 | 7/1992 |
| EP | 0627165 A1 | 12/1994 |
| FI | PCT/FI89/00240 | 7/1991 |
| FR | 1.533.177 | 1/1966 |
| FR | 1533177 | 7/1968 |
| FR | EP 0406 103 | 1/1991 |
| GB | EP 0335023 | 10/1989 |
| JP | 2-88510 | 3/1990 |
| JP | 2088510 | 3/1996 |
| JP | 10-265315 | 10/1998 |
| JP | 119 3206 | 7/1999 |
| JP | 11-193206 | 7/1999 |
| JP | 2000239115 | 5/2000 |
| US | PCT/US83/01433 | 3/1984 |
| US | PCT/US90/05246 | 3/1992 |
| US | EP92100010.5 | 7/1992 |
| US | PCT/US93/05054 | 12/1993 |
| US | PCT/US93/07143 | 3/1994 |
| US | EP94107844.6 | 12/1994 |
| US | PCT/US95/03572 | 9/1995 |
| WO | WO-84/01089 | 3/1984 |
| WO | WO-91/09527 | 7/1991 |
| WO | WO-92/03055 | 3/1992 |
| WO | WO-93/09672 | 5/1993 |
| WO | WO-93/24013 | 12/1993 |
| WO | WO-94/04034 | 3/1994 |
| WO | WO-95/25430 | 9/1995 |
| WO | WO-01/82704 A2 | 12/2001 |

OTHER PUBLICATIONS

Stamets, Paul. Printout of webpage from www.fungi.com (Fungi Perfecti, Shelton, WA), Dec. 1999.

Booth et al., Potential of a Dried Rice/Mycelium Formulation of Entomopathogenic Fungi to Suppress Subterranean Pests in Smal Fruits, Biocontrol Science and Technology, 8: pp. 197–206 (1998).

Rombach et al., Infection of Rice Brown Planthopper, Nilaparvata lugens (Homoptera: Delphacidae), by Field Application of Entomopathogenic Hyphomycetes (Deuteromycotina), Environmental Entomol. 15(5): pp. 999–1110 (1986).

(List continued on next page.)

Primary Examiner—Neil S. Levy
(74) Attorney, Agent, or Firm—William R. Hyde

(57) ABSTRACT

The present invention utilizes the non-sporulating mycelial stage of insect-specific parasitic fungi. The fungus can be present on grain, attracting the pest, and also infecting it through digestion. More than one fungus can be used in combination. The matrix of fungi can be dried or freeze-dried, packaged and reactivated for as an effective bioinsecticide.

8 Claims, No Drawings

OTHER PUBLICATIONS

Maniania, Evaluation of three formulations of Beauveria bassiana (Bals.) Vuill. for control of the stem borer Chilo partellus (Swinhoe) (Lep., Pyralidae), Journal App. Entomol. 115: pp. 266–272 (1993).

Auld, Mass production, formulation and application of Fungi as biocontrol agents, Biological Control of Locusts and Grasshoppers (Lomer and Prior, eds.), Proceedings of the International Institute of Tropical Agriculture Cotonou, Republic of Benin, CAB International, Wallingford, pp. 219–229 (1991).

Pereira et al., Alginate and Cornstarch Mycelial Formulations of Entomopathogenic Fungi, Beauveria bassiana and Metarhizium anisopliae, J. Econ. Entomol. 84 (6): pp. 1657–1661 (1991).

Pereira et al., Growth of Beauveria bassiana in Fire Ant Nest Soil with Amendments, J. Invert. Pathol. 62: pp. 9–14 (1993).

Wells et al., Virulence of Four Fungal Pathogens to Coptotermes formosanus (Isoptera: Rhinotermitidae), J. Entomol. Sci. 30 (2): pp. 210–215 (1995).

Starratt et al., Aggregation of the confused flour beetle, Tribolium confusum, elicited by mycelial constituents of the fungus Nigrospora sphaerica, J. Insect Physiol. 17: pp. 407–414 (1971).

Ferron, Modification of the development of Beauveria tenella mycosis in Melolontha melolontha larvae, by means of reduced doses of organophosphorus insecticides, Ent. exp. & appli. 14: pp. 457–466 (1971).

Hanel et al., Preliminary field tests on the use of Metarhizium anisopliae for the control of Nasutitermes exitiosus (Hill) (Ispptera: Termitidae, Bull. ent. Res. 73: pp. 305–313 (1983).

Cornelius et al., Responses of Coptotermes formosanus and Reticulitermes flavipes (Isoptera: Rhinotermitidae) to Three Types of Wood Rot Fungi Cultured on Different Substrates, J. Econ. Entomol. 95 (1): 121–128 (2002).

Matsuo et al., Responses of the Termite Coptotermes formosanus (Shiraki) to Extract Fractions from Fungus–infected Wood and Fungus Mycelium, 15 Mater. Org. 29: pp. 225–238 (1974).

Kelley–Tunis et al., Activity of Entomopathogenic Fungi in Free–Foraging Workers of Camponotus pennsylvanicus (Hymenoptera: Formicidae), Journal of Economic Entomology, Aug., 1995, pp. 937–943, vol. 88 No. 4, Entomological Society of America, USA.

* cited by examiner

MYCOPESTICIDES

BACKGROUND OF THE INVENTION

1. Field of the Invention

The present invention relates to the use of fungal mycelium as a biopesticide. More particularly, the invention relates to the control and destruction of insects, including carpenter ants, fire ants, termites, flies, beetles, cockroaches and other pests, using fungal mycelia as both attractant and infectious agent.

2. Description of the Related Art

The use of chemical pesticides is the cause of many secondary environmental problems aside from the death of the targeted pest. Poisoning of soil and underlying aquifers may occur, along with pollution of surface waters as a result of runoff. Increases in cancer, allergies, immune disorders, neurological diseases and even death in agricultural workers and consumers have been attributable to the use of pesticides. Chemical pesticides are increasingly regulated and even banned as a health risk to citizens. Communities are increasingly in need of natural solutions to pest problems.

Compounding these problems, many pest type or vermin insects have developed a broad spectrum of resistance to chemical pesticides, resulting in few commercially available pesticides that are effective without thorough and repeated applications. In addition to being largely ineffective and difficult and costly to apply, chemical pesticides present the further disadvantage of detrimental effects on non-target species, resulting in secondary pest outbreaks. It is believed that widespread use of broad-spectrum insecticides often destroys or greatly hampers the natural enemies of pest species, and pest species reinfest the area faster than non-target species, thereby allowing and encouraging further pest outbreaks. There is therefore a particular need for natural alternatives.

Biological control agents have been tried with varying results. Bacteria such as *Bacillus thurigenesis* are used with some success as a spray on plants susceptible to infestation with certain insects. Fungal control agents are another promising group of insect pathogens suitable for use as biopesticides for the control of insects. However, limited availability, cost and reliability have hampered the development of such fungal control agents. Host range and specificity has been a problem as well as an advantage; a fungal pathogen that is virulent and pathogenic to one insect species may be ineffective against other species, even those of the same genus. However, some success has been demonstrated.

The typical lifecycle of a pathogenic fungi control agent involves adhesions of the spore(s) to the host insect cuticle, spore germination and penetration of the cuticle prior to growth in the hemocoel, death, saprophytic feeding and hyphal reemergence and sporulation. For example, U.S. Pat. No. 4,925,663 (1990) to Stimac discloses *Beauveria bassiana* used to control fire ants (Solenopsis). Rice, mycelia and spores (conidia) mixture may be applied to fire ants or used as a bait and carried down into the nest, thereby introducing spores. U.S. Pat. No. 4,942,030 (1990) to Osborne discloses control of whiteflies and other pests with *Paecilomyces fumosoroseus* Apopka spore conidia formulations. The *Paecilomyces fungus* is also useful for control of Diptera, Hymenoptera, Lepidoptera, Bemisia, Dialeurodes, Thrips, Spodoptera (beet army worm), Leptinotarsa (Colorado potato beetle), Lymantria (Gypsy moth), Tetranychus, Frankliniella, Echinothrips, Planococcus (*Citrus mealybug*) and Phenaococcus (*Solanum mealybug*). U.S. Pat. No. 5,165,929 (1992) to Howell discloses use of *Rhizopus nigricans* and other fungus in the order Mucorales as a fungal ant killer. U.S. Pat. No. 5,413,784 (1995) to Wright et al. discloses compositions and processes directed to the use of *Beauveria bassana* to control boll weevils, sweet potato whiteflies and cotton fleahoppers. U.S. Pat. No. 5,683,689 (1997) to Stimac et al. discloses conidial control of cockroaches, carpenter ants, and pharaoh ants using strains of *Beauveria bassana* grown on rice. U.S. Pat. No. 5,728,573 (1998) to Sugiura et al. discloses germinated fungi and rested spore termiticides of entomogenous fungus such as *Beauveria brongniartii, Beauveria bassana, Beauveria amorpha, Metarhizium anisopliae* and *Verticillium lecanii* for use against insects such as termites, cockroaches, ants, pill wood lice, sow bugs, large centipedes, and shield centipedes. U.S. Pat. No. 5,989,898 (1999) to Jin et al. is directed to packaged fungal conidia, particularly Metarhizium and Beauveria. The scientific journal literature also discusses similar uses of conidial preparations.

One disadvantage to such approaches is that the fungal lifecycle may be particularly sensitive to and dependent upon conditions of humidity, moisture and free water, particularly during the stages of germination, penetration of the cuticle prior to growth, and hyphal reemergence and sporulation after death of the insect.

Another continuing problem with existing techniques has been inconsistent bait acceptance. Baits are often bypassed and left uneaten. Such may be a particular problems with insects such as termites, as opposed to house ants and cockroaches, because it is usually not possible to remove competing food sources for termites. Attractants and feeding stimulants have sometimes increased the consistency of bait acceptance, but such increases cost and complexity, and there remains a continuing need for improved baits with improved bait acceptance.

A particular disadvantage with conidial fungal insect preparations becomes apparent from U.S. Pat. No. 5,595,746 (1997) to Milner et al. for termite control. *Metarhizium anisopliae* conidia are disclosed and claimed as a termite repellant in uninfested areas and as a termite control method in infested areas. The difficulties of utilizing conidia or conidia/mycelium as a bait and/or contact insecticide are readily apparent when considering that conidia are effective as an insect repellant to termites and are repellant in varying degrees to most or all targeted insect pests. A repellant, of course, does not facilitate use as a bait or contact insecticide. This may be a factor in explaining why fungal insecticides have all too often proven more effective in the laboratory, where conidia may be unavoidable in the testing chamber or even directly applied to insects, than in the field.

U.S. Pat. No. 4,363,798 (1982) to D'Orazio is for termite baits utilizing brown rot fungus as an attractant and toxicant boron compounds in mixtures effectively sufficient to kill termites without creating bait shyness. Brown-rot inoculated wood which is ground and mixed with cellulosic binder and boron compounds. Such an approach has the disadvantage of utilizing toxic boron compounds. In addition, the cultured mycelium must be further processed.

There is, therefore, a continuing need for enhancing the effectiveness of entomopathogenic (capable of causing insect disease) fungal products and methods. There is also a need for enhancing the attractiveness of such fungal pesticides to insects. There is also a need for improved packaging, shipping and delivery methods.

In view of the foregoing disadvantages inherent in the known types of fungal biocontrol agents, the present invention provides improved fungal biocontrol agents and methods of using such agents.

SUMMARY OF THE INVENTION

The present invention offers an environmentally benign approach to insect control by attracting the insects who ingest latent preconidial mycelium (which may be fresh, dried or freeze-dried) which then infects the host. The preconidial mycelium is both the attractant and the pathogenic agent. The infected insects carrying the fungal hyphae become a vector back to the central colony, further dispersing the fungal pathogen. Mycelium is grown in pure culture using standard fermentation techniques for in vitro propagation. The fermented mycelia is diluted and transferred into a sterilized grain or a mixture of sterilized grains. Once inoculated, the fermented mycelia matures to a state prior to conidia formation. The preconidial mycelium may be utilized as is or may be arrested in its development through flash chilling (or by other means such as air-drying or refrigeration) and packaged in spoilage-proof or sealed packages. The end-user facilitates opening the package and placing the exposed mycelia-grain contents in the vicinity of recent pest activity.

The present invention thus provides improved products and methods wherein the fungal mycelium acts as bait and attractant and as an ingested or food insecticide, palatable enough that insects will readily consume it even in the presence of competing food sources, with high recruitment of other insects among social insects that exhibit such behavior. This results in multiple visits to a highly attractive pathogenic bait, thereby providing effective individual insect and/or colony inoculation.

The present invention further provides these and other advantages with improved control of insect pests using fungal insecticidal compositions (mycopesticides) having strong attractant properties and placing these attractant mycopesticides in or around an object or area to be protected. The present invention also provides insecticidal baits which use, as a toxicant, relatively innocuous, naturally occurring materials as the active agent, so as to control insects without undue effect on the ecology. Finally, by actively avoiding the use of conidia, the time and expense of raising conidial stage mycelium and/or separating conidia is avoided.

Still further objects and advantages of the present invention will become more apparent from the following detailed description and appended claims.

Before explaining the disclosed embodiments of the present invention in detail, it is to be understood that the invention is not limited in its application to the details of the particular products and methods illustrated, since the invention is capable of other embodiments. Also, the terminology used herein is for the purpose of description and not of limitation.

DESCRIPTION OF THE PREFERRED EMBODIMENTS

The present invention provides improved mycopesticides (fungal mycelia utilized as insect biopesticides). The attractiveness of fungal mycelia to many species is well known. Black Angus cows have been observed running uphill (a rare event) to reach spent Oyster mushroom mycelium on straw. Cultured mycelia such as Morel mycelium is considered a delicacy when added to human foods; gourmet mushrooms themselves are a form of mycelium fruitbody. Indeed, the attractiveness of mycelial scents is to a great degree responsible for the fresh and refreshing scent of a forest after a rain, a result of the mushroom mycelia responding to the humid conditions with rapid growth. Mycelium is also known to be highly attractive to insects. Certain ants, termites and wood-boring beetles are known to cultivate and raise fungal mycelium as an exclusive food source ("ambrosia fungi") and mycelium is a preferred food source of many insect species. As discussed above, brown rot mycelium (the mycelial stage of a wood-rotting type of fungus that produces polypore mushrooms) has been used as an attractant for termites.

However, for insect control typical use of fungal pathogens has involved use of either conidia (spores) or a mixture of conidia and mycelium as a "contact insecticide" control agent. Such conidial contact insecticides suffer two major disadvantages: 1) conidia and conidia/mycelium preparations are to some degree unattractive or even repellant to insects; and 2) such conidia preparations are highly dependent on free water or humid conditions for gestation and infestation during the typical life cycle of an insect fungal control agent. Furthermore, conidia have been found to be more effective against "stressed" insects and/or insect populations than against healthy insects and populations. For these and other reasons, conidia of entomopathogenic fungi have often been much more effective under laboratory conditions than in the field.

Noting that conidia have been utilized as a repellant for termites, further investigation of the preconidial and conidial stages were undertaken. The preconidial stage is the vegetative stage of the fungus, prior to the formation of structures leading to the release of air-borne spores (which is distinguished from fragmentation of hyphae which can become airborne if dried). Those skilled in the art will recognize that mycelia or mycelial hyphal fragments may form structures such as arthospores (a preconidial structure imbedded within the mycelia) and such should be considered a "preconidial mycelium" as discussed elsewhere. It was found that the "fragrance signature" of the mycelium is a strong attractant to insects, but only prior to conidia formation. After conidia formulation, the conidia/mycelium was found to be repellant to insects such as carpenter ants. The odor was found to be similarly pleasing to humans when preconidial and repellant when post-conidial. It was noted such fragrance signatures are "washed away" or lost when mycelium is grown via liquid fermentation. It was also noted liquid fermentation utilizing a typical fermentor with bubbled air mixing will promote conidia formation, with such conidia production being even further promoted by the common commercial practice of utilizing bubbled oxygen.

It was further found that fungal control agents are much more effective when preconidial mycopesticidal mycelium is ingested by the targeted insect as compared to conidia or post-conidial mycelium/conidia offered to targeted insects for the purpose of infection by contact. Whereas conidia have little or no effect by ingestion or vapor, preconidial mycelium has proven to be highly effective by ingestion, the mycelial hyphae already being in a state of active growth when ingested. Furthermore, whereas conidial preparations are more dependent upon humidity in the insect environments, a preconidial mycopesticidal mycelium which is eaten by an insect is dependent upon humidity only in the immediate vicinity of the mycelium, the humidity of the mycelium of course being much more easily controlled than in the wider general insect environment.

It has further been found that the preconidial stage can be maintained provided carbon dioxide ($CO_2$) levels are maintained at an elevated level. The $CO_2$ levels preferably range from 2,000–200,000 ppm, more preferably in the range of 10,000–50,000+ppm. Once exposed to fresh air, the mycelium can produce conidia in just a few days. By preventing conidial formation, the mycelium continues to accumulate mycelial biomass (sans conidia). Even after maturation, the mycopesticidal mycelium may be maintained in a pre-conidial state via elevated carbon dioxide levels. This prevention of conidia formation is an active component in this technology, as conidia formation is actively avoided.

Mycopesticidal mycelium is grown in pure culture using standard fermentation techniques well established for in vitro propagation. The fermented mycelia is diluted and transferred into a sterilized grain or a mixture of sterilized grains (rice, wheat, rye, oat, millet, sorghum, corn, barley, etc.). The grain is pressure steam-sterilized at 1 kg/$cm^2$ (15 psi) for several hours. The master broth is transferred aseptically manually or by using peristaltic pumps into the sterilized grain. Growth mediums containing sawdust, sugar cane, corn cobs, cardboard, paper or other substances containing cellulose may be utilized for cellulose loving insects such as termites if desired. A variety of containers are used for incubation, including high-density polyethylene and polypropylene bags, glass and polypropylene jars, metal containers, etc.). Use of such containers provides a convenient method of maintaining high $CO_2$ levels, as the growing mycelium gives off carbon dioxide. $CO_2$ levels will rise to acceptable levels for use in the present invention even if filter patches, disks or materials are utilized to allow some gas exchange. Alternatively, grow rooms may be maintained at high $CO_2$ levels. Further information on such culture techniques may be found in the applicant's books, *Growing Gourmet and Medicinal Mushrooms* (1993, 2000) and The *Mushroom Cultivator* (1983) (with J. Chilton), and in standard microbiology manuals.

Once inoculated, the mycelia on grain matures to a state prior to conidia formation and may be utilized fresh or metabolically arrested or developmentally arrested through flash chilling (freeze-drying), drying, refrigeration or by other means. It will be understood that such metabolic arresting of development may encompass either a slowing of metabolism and development (such as refrigeration) or a total suspension or shutdown of metabolism (freeze-drying, air-drying and cryogenic suspension). When freeze-drying, drying or other known methods of arresting development are utilized, it is essential that freeze-drying or other methods occur at an early stage in the life cycle of these fungi before the repellant spores are produced. The mycelium-impregnated grain media may then be fragmented and packed in appropriate containers for commerce. Fresh mycelium may be shipped in growing containers such as jars or spawn bags, which allows easy maintenance of a high carbon dioxide atmosphere and maintenance of sterile conditions during shipping. It is preferable that the mycelium be utilized or processed while vigorous, before it "over-matures" and becomes less viable for lack of new food to digest and accumulation of waste products.

When the freeze-dried or dried mycelium is reactivated via rehydration, the mycelium is preferably allowed to slowly rehydrate through controlled absorption of atmospheric humidity, with the result that the mycelium "wakes up" and wicks into the air. This is a totally different response from immersion, which often results in bacterial contamination and souring, as the freeze-dried mycelium suffers when immersed in water. Such rehydration and reactivation may be carried out on a large scale through high humidity atmosphere, or may be accomplished by an end user through use of wet materials such as sponges, wicking materials and/or other evaporative materials or by atmospheric absorption of humidity from a remote water reservoir. Such end user rehydration may be carried out in any suitable container or a bait box if desired. Warming is suitable for reactivation of refrigerated materials; it is preferred that the mycelium not be refrigerated for extended lengths of time.

Novel features of the invention include the use of a vector of parasitization that relies on hyphal fragments, not spores or conidia; the use of a single mycelium as both attractant fungus and pathogen; the use of high levels of $CO_2$ to grow and maintain preconidial mycelium; and the preferred use of various methods to arrest development at the preconidial stage to facilitate growth, packaging, shipping and convenient application by an end user. More than one fungus can be used to create a matrix of characteristics to increase usefulness as a natural pesticide.

In general, preferred mycopesticidal species as pathogens are somewhat slow-acting (that is, not immediately fatal), so as to avoid bait shyness and to avoid learning effects in social insects before individuals have distributed mycelium to other members of the colony. In many applications it may be preferable to utilize a mixture or matrix of several species of entomopathogenic fungus with different characteristics, maturation and growth rates, preferred conditions, virulence and pathogenicity, time to insect death, etc., while in other applications a single species may be preferred. Similarly, with reference to a single species, a mixture of strains or a single strain may be utilized. Those skilled in the art will recognize that such characteristics can be selected for utilizing known techniques and bioassays. The mycopesticides disclosed herein may also be optionally enhanced by the use of other baits, attractants, arrestants, feeding stimulants, sex pheromones, aggregating pheromones, trail pheromones, etc.

There are numerous entomogenous and entomopathogenic fungal species known. Those skilled in the art will recognize that the above preconidial fungi methods and products may be favorably applied to all such insecticidal fungal species, and it is the intent of the inventor that the invention be understood to cover such. Suitable entomopathogenic fungi include Metarhizium, Beauveria, Paecilomyces, Hirsutella, Verticillium and other fungi imperfecti, the Entomophthoracae and other Phycomycetes, and sexually reproducing fungi such as Cordyceps and other Ascomycetes.

By way of example, but not of limitation, preferred mycopesticides include Metarhizium anisopliae ("green muscarine" for pests such as carpenter ants, including *Camponotus modoc, C. vicinus, C. ferrugineus, C. floridanus, C. pennslyvanicus, C. herculeanus, C. varigatus* and *C. vicinus*, fire ants (*Solenopsis invicta* and *Solenopsis richteri*, termites, including Coptotermes, Reticulitermes, Cryptotermes, Incisitermes, Macrotermes and Odontotermes, pasture scarabs such as *Adoryphorus couloni*, spittle bug *Mahanarva posticata*, corn earworm *Helicoverpa zea*, tobacco hornworm *Manduco sexta*, sugar cane froghopper, pill wood lice, sow bugs, large centipedes, shield centipedes, wheat cockchafer, beetle grubs, greenhouse pests such as Coleoptera and Lepidoptera, etc.); *Metarhizium flaviride* (grasshoppers and locusts); *Beauveria bassana* ("white muscarine" for termites including Formosan termites, carpenter ants, fire ants, pharaoh ants, cockroaches, whiteflies, thrips, aphids, mealybugs, boll weevils, sweet potato whiteflies, cotton fleahoppers, European and Asiatic corn borers and larvae of other Lepidoptera, codling moth, chinch bug, soft-bodied insects in the orders Homoptero and Coleoptera, Heteroptera, etc.);

*Beauveria brongniartii* (white grubs and cockchafers, *Hoplochelis marginalis, Melolontha melontha*); *Pacilomyces fumosoroseus* (whiteflies, thrips, aphids, spider mites, mealybugs, beet army worm, Colorado potato beetle, Gypsy moth, etc.); *Verticillium lecanii* (greenhouse pests, whiteflies and aphids); *Hirsutella citriformis* (rice brown planthopper); *Hirsutella thompsoni* (citrus rust mite); and the wide variety of Cordyceps for baiting and killing pests such as beetles, flies, cockroaches, earwigs (*Forficula auricularia*), carpenter ants and various other insect pests, including *Cordyceps variabilis*, including imperfect forms (fly larvae, Xylophagidae family of the Deptera order), *Cordyceps facis* and *C. subsessilis*, (beetle larvae in the coleopteran family, Scarabaeidae), *Cordyceps myrmecophila* (ants); *Cordyceps sphecocephala* (wasps), *Cordyceps entomorrhiza* (beetle larvae), *Cordyceps gracilis* (larvae of beetles and moths), *Cordyceps militaris, Cordyceps washingtonensis, Cordyceps melolanthae* (beetles and beetle grubs), *Cordyceps ravenelii* (beetle grubs), *Cordyceps unilateralis* (ants, carpenter ants, bees and wasps) and *Cordyceps clavulata* (scale insects).

With regard to the sexually reproducing Cordyceps, preconidial or pre-sporulation refers to the pre-fruiting state. The term "preconidial" has a somewhat different meaning than with most other entomopathogenic fungi, as Cordyceps is a "fungi perfecti" or mushroom fungi, whereas the other non-mushroom fungi referred to herein are the more primitive "fungi imperfecti." Some or all Cordyceps fungi are believed to be anamorphic or dimorphic and have conidial stages within the imperfect fungal genera including Beauveria, Metarhizium, Paeciloymyces, Hirsutella, Verticillium, Aspergillus, Akanthomyces, Desmidiospora, Hymenostilbe, Mariannaea, Nomuraea, Paraisaria, Tolypocladium, Spicaria (=Isaria) and Botrytis. For example, *C. subsessillis* is the perfect form of *Tolypocladium inflatum*, an anamorph (imperfect) form which produces cyclosporin. Hodge et al., *Tolypocladium inflatum* is the anamorph of *Cordyceps subsessilis*. Mycologia 88(5): 715–719 (1996). *Cordyceps militaris* (Fr.) Lk. is also thought to be dimorphic, the conidial stage of which is believed to be a Cephalosporium. DNA studies are expected to better elucidate these relationships. As a further complexity, in addition to possible anamorphs and dimorphs, Cordyceps species also demonstrate nonsexual imperfect stages of development. As used herein, unless otherwise specified, preconidial Cordyceps refers to the pre-sporulation mycelial stage of the Cordyceps mushrooms, including any preconidial imperfect stages, but not any conidia bearing imperfect stages.

For initial experimentation, a *Metarhizium anisopliae* from naturally occurring sources and the carpenter ant were selected. *M. anisopliae* was obtained from a public culture collection and used without further selection or virulence and/or pathogenicity; a publicly available strain free of proprietary or patent restrictions on use was selected as offering a preferred source and a more demanding initial test than strains selected for specific pathogenicity. It will be understood, of course, that strains selected for specific characteristics and pathogenicity against specific insects will in general offer the best mode of practicing the invention. The carpenter ant offered several advantages: ants are typically more resistant to spores than termites and other insects, carpenter ants are a very destructive pest, the effect on other ant species could also be viewed, and the applicant enjoyed easy access to an experimental site as his residence was in danger of collapse due to long term structural infestation by carpenter ants.

EXAMPLE 1

*Metarhizium anisopliae* was grown in pure culture using standard fermentation techniques and diluted and aseptically transferred to grain (rice) which had been pressure steam-sterilized at 1 kg/cm2 (15 psi) utilizing. The fermented mycelia matured to a state prior to conidia formation and the fungus colonized grain was offered at the site of debris piles caused by carpenter ants at the 1,100–1,200 sq. ft. house of the applicant's residence located in Shelton, Wash., U.S.A. Approximately 10–20 grams of preconidial mycelium of *Metarhizium anisopliae*, grown on autoclaved rice and having been incubated for two weeks, was presented at the location of debris piles next to the interior face of an exterior wall within the house. The non-sporulating mycelium was presented on dollhouse dinner dish, and left exposed to the air. Later that night, the applicants' daughter urgently awoke the applicant when she observed carpenter ants feasting en masse on the non-sporulating mycelium of the presented Metarhizium. The applicant and his family observed approximately a dozen carpenter ants ingesting mycelium and retreating into the wall, carrying the infectious mycelium with them. In a week's time, the carpenter colony became inactive, killing the nest of ants, and no evidence of carpenter ant activity was observed henceforth, saving the structure from further structural damage. Months later, the ecological niche once occupied by the carpenter ants was taken over by common household Sugar and Honey ants which were unaffected by the *Metarhizium anisopliae*.

EXAMPLE 2

Cultivate strains of Metarhizium, Beauveria and Cordyceps on grain as above under high $CO_2$ conditions to produce preconidial mycelium. Freeze-dry and rehydrate. Apply as bait and pathogen at locations infested by insects such as carpenter ants, termites, beetles, flies, fire ants, cockroaches and other insect pests and vermin.

EXAMPLE 3

Drill one or more holes into a termite colony mound or tree mound. Insert entomopathogenic preconidial mycopesticide mycelium into holes. Cover holes to prevent entry of marauding ants.

No limitations with respect to the specific embodiments disclosed herein is intended or should be inferred. While preferred embodiments of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

I claim:

1. A method for attracting social insects selected from the group consisting of carpenter ants, fire ants, Coptotermes Formosan termites and Reticulitermes termites, consisting essentially of treating an infested locus with an effective dose of a preconidial mycelia of an entomopathogenic fungi prior to the formation of structures leading to the release of air-borne spores, wherein the preconidial mycelia is *Metarhizium anisopliae* grown on a solid culture media selected from the group consisting of grains, sawdust, sugar cane, corn cobs, cardboard, paper and cellulose containing substances, and wherein the preconidial mycelia is provided in an amount sufficient to act as both an insect attractant and an insect pathogen.

2. The method for attracting social insects of claim 1 wherein hyphal fragments of the preconidial mycelia act as an initial vector of parasitization.

3. The method for attracting social insects of claim 1, wherein the preconidial mycelia is a *Metarhizium anisopliae* effective against carpenter ants.

4. The method according to claim 1 wherein the preconidial mycelia is metabolically arrested and subsequently metabolically reactivated.

5. The method according to claim 4 wherein the preconidial mycelia is metabolically arrested by a method selected from the group consisting of freeze-drying and drying and is subsequently metabolically reactivated by rehydration.

6. The method according to claim 4 wherein the preconidial mycelia is metabolically arrested by a method selected from the group consisting of refrigeration and cryogenic suspension and subsequently metabolically reactivated by warming.

7. A method for attracting carpenter ants, consisting essentially of treating an infested locus with an effective dose of a preconidial mycelia of an entomopathogenic fungi prior to the formation of structures leading to the release of air-borne snores, wherein the preconidial mycelia is provided in an amount sufficient to act as both an insect attractant and an insect pathogen, wherein the preconidial mycelia is a *Metarhizium anisopliae* grown on a solid culture media, wherein the preconidial fungal mycelia is metabolically arrested by a method selected from the group consisting of freeze-drying, drying, refrigeration and cryogenic suspension and subsequently metabolically reactivated by a method selected from the group consisting of rehydration and warming, and wherein the solid culture media is selected from the group consisting of grain, sawdust, sugar cane, corn cobs, cardboard and paper.

8. A method for attracting carpenter ants consisting essentially of treating an infested locus with an effective dose of a preconidial mycelia of an entomopathogenic fungi prior to the formation of structures leading to the release of air-borne spores, wherein the preconidial mycelia is a *Metarhizium anisonliae* effective against carpenter ants, wherein the preconidial mycelia is provided in an amount sufficient to act as both an insect attractant and an insect pathogen and wherein the preconidial mycelia is grown on a solid culture media is selected from the group consisting of grain, sawdust, sugar cane, corn cobs, cardboard and paper.

* * * * *

UNITED STATES PATENT AND TRADEMARK OFFICE
CERTIFICATE OF CORRECTION

| | | |
|---|---|---|
| PATENT NO. | : 6,660,290 B1 | Page 1 of 1 |
| APPLICATION NO. | : 09/678141 | |
| DATED | : December 9, 2003 | |
| INVENTOR(S) | : Paul Edward Stamets | |

It is certified that error appears in the above-identified patent and that said Letters Patent is hereby corrected as shown below:

On Page 1:
    Item (73), "Assignee: Myco Pesticides LLC, Grand Rapids, MI (US)" should read
        --Assignee: MYCOSYS, LLC, Shelton, WA (US)--
    Item (22), "Filed: Oct. 3, 2000" should read --Filed: Oct. 4, 2000--.

Signed and Sealed this

Eighth Day of May, 2007

JON W. DUDAS
*Director of the United States Patent and Trademark Office*